United States Patent
Rubio et al.

(10) Patent No.: US 6,764,699 B2
(45) Date of Patent: Jul. 20, 2004

(54) CORN TORTILLAS WITH IMPROVED TEXTURE RETENTION USING AN ENZYME BLEND IN NIXTAMALIZED CORN FLOUR

(75) Inventors: Manuel J. Rubio, Miami Beach, FL (US); Roberto Contreras, Guadalupe (MX); Marco A. Baez, Centro. Queretaro Qro. (MX)

(73) Assignee: Roberto Gonzalez Barrera, Delegacion Miguel Hidalgo (MX)

( * ) Notice: Subject to any disclaimer, the term of this patent is extended or adjusted under 35 U.S.C. 154(b) by 0 days.

(21) Appl. No.: 10/167,511

(22) Filed: Jun. 13, 2002

(65) Prior Publication Data

US 2003/0059496 A1 Mar. 27, 2003

Related U.S. Application Data

(63) Continuation-in-part of application No. 09/729,196, filed on Dec. 5, 2000, now abandoned.

(51) Int. Cl.$^7$ ............................................. A23L 1/105
(52) U.S. Cl. ....................................................... 426/52
(58) Field of Search ............................. 426/18, 44, 28, 426/61, 653, 549, 31

(56) References Cited

U.S. PATENT DOCUMENTS

| | | |
|---|---|---|
| 5,514,404 A | 5/1996 | Zimmerman et al. ....... 426/549 |
| 6,265,013 B1 | 7/2001 | Martinez-Montes et al. ......................... 426/622 |

*Primary Examiner*—Keith Hendricks
(74) *Attorney, Agent, or Firm*—Young & Thompson

(57) ABSTRACT

Corn masa dough texture and tortilla flexibility are improved by adding to the nixtamalized corn flour, an enzyme blend comprising commercial hemicellulase and/or cellulase. The enzyme preparation has a positive effect on dough texture and improvement in tortilla elasticity and ductility during commercial storage. The combination of the enzyme blend and the method for dough and tortilla preparation can enhance conventional additives to delay corn tortilla hardening during storage.

8 Claims, No Drawings

CORN TORTILLAS WITH IMPROVED TEXTURE RETENTION USING AN ENZYME BLEND IN NIXTAMALIZED CORN FLOUR

This application is a continuation-in-part of now abandoned application Ser. No. 09/729,196, filed on Dec. 5, 2000, the entire contents of which are hereby incorporated by reference.

BACKGROUND OF THE INVENTION

1. Field of the Invention

This invention relates to a method for improving the Theological properties of corn packaged-tortillas by using commercial Xylanase with antimicrobial acidic-additives during tortilla making.

2. Description of Related Art

High-quality masa flour can be produced by conventional techniques only if the food-grade dent corn has the following characteristics: uniformity in kernel size and hardness, low stress-cracks and kernel damage and ease of pericarp removal during the lime-water cooking process. Nixtamalized corn flour (NCF) is produced by alkaline cooking of corn, washing, grinding the nixtamal and drying to give corn masa flour. This flour is sieved and blended for different product applications and it is usually supplemented with additives before packaging for commercial table tortilla and snack production. MASECA is the main brand flour in the US and Latin America, followed by Minsa, Agroinsa, Ill. Cereal Mills (Cargill) and Quaker Oats (Sustain, 1997).

Although the pericarp or bran is partially removed during the alkaline-cooking and washing process stages, there is still fiber left from the corn kernel (U.S. Pat. No. 4,513,018; Montemayor & Rubio, 1983, Ramirez & Alvarez, 1995). According to Watson (1987), the corn pericarp makes up 5–6% of the kernel dry weight. It also contains 67% hemicellulose, 23% cellulose and 0.6% soluble-fiber (soluble-hemicellulose). Unlike whole wheat, in which soluble fiber amounts to 11% of the total fiber, the corn soluble fiber is negligible (1%). Primary cell walls from the aleurone and starchy endosperm (83% dry weight) consist predominantly of arabinoxylan, β-glucan and some cellulose. It is estimated that mainly insoluble fiber in the pericarp and endosperm make up 78% of the total dietary fiber (9.5% in the kernel dry-weight).

Arabinoxylans are complex polymers (20,000–170,000 daltons) with a linear backbone of (1,4)-β-xylopiranosyl units to which substituents are attached through 02 and 03 atoms of the xylosil residues (mainly, α-L-arabinofuranosyl; Fincher and Stone, 1986). A high degree of arabinosylation will increase its water solubility and more than 20% of the water in wheat-flour dough is associated with arabinoxylans. This polymer is apparently linked to the cellulose skeleton in the corn cell wall by ester linkage cross-bonding through ferulic and diferulic acid.

Nixtamalized corn flour or masa flour can contain from 7–9% of total dietary fiber or bran and 6–8% mainly consists of insoluble fiber on a dry-weight basis (Sustain, 1997). Dietary fiber of the new generation can surpass the functional and sensory qualities of the standard dietary fibers (e.g., commercial source of wheat bran can be removed of its starch, gluten and phytic acid). Due to its new fiber structure and its capillary effect the new fiber has good water binding capacity (twicefold) and a positive effect on baked goods freshness (e.g., Vitacel-brand name).

Haarasilta et al. (U.S. Pat. No. 4,990,343), Báez-Vásquez and Schoefield (1993) and Tanaka et al. (U.S. Pat. No. 5,698,245) have proposed that the use of endo and exo-hemicellulases causes decomposition of wheat insoluble fiber. Van Der Wouw et al (U.S. Pat. No. 6,066,356) also reported the use of arabinoxylanases to degrade the water-insoluble-solids from maize, in the preparation of feed or food (degermed maize and debranned wheat for bread).

Native Cellulose and Hemicellulose would render the dough non-homogeneous and affect the dough stretching capacity by preventing the formation of a gluten network (e.g., gliadin which provides elasticity and glutenin which effects viscosity). The enzyme treated bread product has an increased volume, more uniform grain structure, slower aging (retarded staling or retrogradation) and a reduction or replacement in baking additives.

Fiber components of Corn Kernel Parts

| Part | % Dry matter | Fiber Insol. | Hemicellulose | Cellulose | Lignin | Soluble fiber | Fiber Total | % Kernel fiber |
|---|---|---|---|---|---|---|---|---|
| Whole Kernel | 100 | 9.5 | 6.7 | 3 | 0.2 | 0.1 | 9.5 | 100 |
| Starchy Endosperm | 80.9 | 1.0 | — | — | — | 0.5 | 1.5 | 12 |
| Aleurone Endo-Sperm | 2.0 | 50.0 | — | — | — | 25.0 | 75.0 | 15 |
| Germ | 11.0 | 11.0 | 18 | 7 | 1.0 | 3.0 | 14.0 | 16 |
| Pericarp (bran) | 5.3 | 90.0 | 67 | 23 | 0.1 | 0.6 | 90.7 | 51 |
| Tip cap | 0.8 | 95.0 | 70 | — | 2.0 | — | 95.0 | 6 |

Source: Watson, S. A. 1987. Structure and Composition, In: Corn Chemistry and Technology.

The benefit of using a xylanase instead of a traditional hemicellulase (pentosanase) preparation is that there are fewer side activities (e.g., α or β-amylase, β-xylosidase/glucosidase) in the xylanase product. A suitable level of enzymes results in a desirable dough softening without causing stickiness, thereby improving machinability.

Xylanolytic systems (Wong and Saddler, 1992) include xylanases (1,4-β-D-xylan xylanohydrolase, EC 3.2.1.8) and β-xylosidases (1,4-β-D-xylan xylohydrolase, EC 3.2.1.37), the former generally hydrolyse the xylan backbone (endo-type) whereas the latter hydrolyse xylo-oligomers (exo-type). Xylose is not usually the major product and it is typically produced after xylobiose and xylotriose (smallest oligomer). Nonspecific xylanases from Trichoderma spp may attack cellulose and carboxymethylcellulose. Xylanases are classified into two major families (F or 10 and G or 11) of glycosylhydrolases. F10 xylanases are larger, more complex and produce low DP oligosaccharides (less specific); F11 are more specific for xylan (Jeffries, 1996). Low molecular weight xylanases (269–809 amino acid residues) were from *B. Pumilus, B. Subtilis* and *C. Acetobutylicum* (Wong and Saddler, 1992).

The xylanases can be prepared microbiologically by means of fungi and bacteria: *A. Niger* had shown not only arabinose releasing xylanase activity but also a xylotriose one, Trichoderma spp xylanases had optimal acitivity conditions between 45–65° C. and pH 3.5–6.5, Bacillus spp had alkaline tolerant (up to pH 10) and extreme thermophilic xylanases; and a Thermotoga sp (strain FjSS3-B1) xylanase had a temperature optimum of 105° C. at pH 5.5 and an half-life of 90 min at 95° C.

In recent years there has been a growing interest in the use of xylanase enzymes in the paper, pulp (enhance beatability and binding ability), food and feed industries. The use of xylanases (with or without cellulase and pectinase) has been proposed for clarifying juices and wine, for extracting coffee, plant oils and "starch", for improving the nutritional properties of agricultural silage, for macerating plant cell walls, for producing food thickeners and for providing "textures to bakery products". The scope for new applications is restricted mainly by the limited availability of specific xylanases with the required purity, properties (ie, pH optima and thermal stability) and action patterns (endo or exo-hydrolytic mechanisms). Commercial xylanase preparation marketed for pulp treatment include Pulpzyme HA (with little cellulolytic activity) from *T. Reesei* and Albazyme from *T. Longibrachiatum*. Crude enzyme preparations containing both hemicellulases and cellulases could be used to improve fibrillation and drainage properties of recycled pulpwood fibers (Wong and Saddler, 1992).

To aid in these developments, simple, reliable and sensitive procedures are required for the quantitative measurement of xylanase in a range of products with trace to high enzyme activity levels. The advent of genetic engineering has allowed the production of very specific enzyme preparations. A range of plant polysaccharides, including starch, β-glucan, arabinoxylan, fructans, as well as starch damage can be measured (McCleary, 1992).

López-Munguía et al. (Mexican patent application: No. 952,200) describes an enzymatic process to produce corn tortillas which retard accelerated staling with texture improvement during four days frozen storage. A fungal α-amylase blend (i.e., commercial enzymes from Novo, Gist Brocades and Genencor International) was added during rehydration of nixtamalized corn flour (0.01 U/kg), and modified the starch during tortilla cooking up to the denaturing temperature (Iturbe-Chiñas et al., 1996).

SUMMARY OF THE INVENTION

The present invention relates to a method of improving the Theological properties of corn packaged-tortilla produced therefrom, by adding to the nixtamalized corn flour an effective amount of an enzyme component (or blend) containing a xylanase. A dough prepared with this flour premix will have advantageous Theological and handling properties and tolerance in a mechanized tortilla machine (Rodotec Ecológica-100; made by Tecnomaíz Gruma, Monterrey, N.L. México). The final tortilla product will keep its flexibility and compressibility, even during extended commercial storage. The corn packaged-tortilla produced according to the invention therefore has less or no need of conventional antistaling or functional additives.

The dough is produced by combining nixtamalized corn flour, water, and a xylanase, with acidic-additives if desired, and mixing and kneading to form a suitable dough for traditional as well as mechanized tortilla production. The invention also comprises a novel packaged-tortilla premix which includes instant masa flour, antimicrobial acidic-additives, and enzyme preparation with a suitable carrier directly incorporated to the flour during its production.

Accordingly, the present invention provides a soft and cohesive dough without causing stickiness during tortilla manufacture. Another object is to provide a packaged-tortilla with improved flexibility and rollability during commercial storage. The main object of the invention is the application of a xylanase to improve the flexibility of packaged-tortillas. The baked product or corn tortilla is made by combining nixtamalized corn flour with a suitable amount of an enzyme preparation, antimicrobial acidic-additives and water for mixing or kneading to produce a soft and cohesive dough without excessive stickiness during mechanized tortilla production.

Preferably, the enzyme blend contains between 100 mg to about 1000 mg of a commercial xylanase per kilogram of corn flour. The packaged-tortilla premix preferably includes antimicrobial acidic-additives (0.5–1% weight based on flour) in combination with the enzyme blend before adding the premix directly to the flour in the production factory.

DETAILED DESCRIPTION OF PREFERRED EMBODIMENTS

A tortilla can be defined as a flat, round, unfermented pancake produced from lime-cooked corn (*Zea Mays* L.). Three basic types of corn products are industrially manufactured: packaged-tortilla, corn and tortilla chips. Many manufacturers use corn masa flour because it does not require much labor, equipment, and processors do not have to pay as much for effluent disposal and control of production practices.

The enzyme blend comprises about 100 mg to about 1000 mg of xylanase per kilogram of corn flour and calculated as xylanase units. A commercial preparation of fungal hemicellulase from *A. Niger* was, kindly provided by Amano Pharmaceutical Co. and another multicomponent hemicellulase by Rhone-Poulenc (Rhodia). A crude cellulase preparation from *T. Longibrachiatum* (Fraction A: mainly with endoxylanase and cellulase activities) was obtained from Biotechnology Center (ITESM, Monterrey, N.L., México: Báez-Vásquez and Schoefield, 1993).

The definitions of the different enzyme activities are defined below:

Xylanase activity (Megazyme International Ireland, Ltd. Ireland). A modified Somogyi-Nelson reducing sugar assay for the measurement of β-xylanase using Wheat Arabinoxylan as substrate (Megazyme assay procedures XYL 9/95:14–15). One unit is the amount of enzyme which produces one micromole of xylose per minute at pH 4.7 and 40° C. (Fraction A: test result 1,400 micromoles-xylose/min-g). The major advantages of this procedure are that the color response with oligosaccharides of increasing degree of polymerisation is stoichiometric; and the assay is very sensitive (10–50 $\mu$g).

Rhodia-Rhone Poulenc reported a minimum xylanase activity (multicomponent hemicellulase) of 4,000 U/gram (4,000 mg-maltose/min-g) or reducing sugar equivalent to 5,850 $\mu$moles-glucose/min-g (DNS assay).

Hemicellulase activity (Amano-Enzyme USA. Co., Ltd.). A Somogyi-Nelson assay was used and one unit is the amount of enzyme which produces reducing sugar equivalent to ten micrograms of xylose per minute at pH 4.5 and 40° C. (Amano-90: test result 109,000 U/gram or 7,270 micromoles-xylose/min-g).

The enzyme preparation may contain xylanase activity functioning both with endo and exomechanisms. They may also contain the following enzyme side-activities: α-amylase (Amano-90), β-xylosidase (Amano-90) and β-glucosidase (Fraction A and Amano-90).

EXAMPLE 1

Preparation of traditional-style corn tortilla, showing the effect of the enzyme blend on corn packaged-tortilla texture A shelf-life study was designed with laboratory corn tortillas stored at room temperature and their flexibility and compressibility changes were recorded simulating seven days storage.

Commercial enzymes were used (Amano-90: code AM-blend from *A. Niger*, and Rhodia-Rhone Poulenc: code RP-blend) as well as a crude cellulase extract from *Trichoderma longibrachiatum* (Fraction A: code A-blend from Biotechnology Center-ITESM). Three enzyme formulations in corn flour were tested: formulation 1 (0 ppm or control), formulation 2 100 ppm and formulation 3 (1000 ppm).

All treatments used nixtamalized corn flour (commercial available type) and a fine dough masa) was manually prepared by rehydration of flour with warm water (30° C.) in a 1:1.25 ratio, and adding a liquid antimicrobial acidic-additive (1% based on flour; Kemin brand). In experiments including enzymes, the appropriate enzyme activity of flour was dissolved in the warm water with additive and manually kneaded during one minute. The dough temperature was about 28° C. and doughballs were manually divided and weighed (25 grams each). Doughballs were plated flat with a manual tortilla machine (Productos Practicos, S.A.) for controlling disk thickness around 0.2-0-3 cm (80-125 mils). Flat dough disks were cooked on a hot plate (185° C.) and after 15 s the tortilla is turned to cook the other face. The exposed side heats up after another 15 s and finally the tortilla is turned again during 15 s until the vapor produced makes it swell. After cooling the tortillas (0.2 cm or 80 mils thick) at room temperature they were packaged in polyethylene bags and sealed for storage.

To evaluate the flexibility effect of all the treatments, tortillas were reheated on a hot plate during 20 s and cooled for five minutes before texture analysis. The flexibility measurement used stainless-steel rods of several diameter (0.5 to 3 cm) and rolling the warmed tortilla in a decreasing size order, recording the rod number at which the tortilla sample just breaks when it is flexed (U.S. Pat. No. 3,730, 732). A more flexible tortilla will just break when it is bent around a smaller rod diameter than a less flexible one. A Compressibility test used a propietary procedure which measured the relative distance when compressing three stored tortillas with a standard weight. This compression test is an uniaxial deformation of a solid food under a constant force and it estimates an instantaneous elastic tortilla deformation. An indirect rollability test consisted in enrolling the warmed tortilla as a cylinder and then recording its average diameter with a Vernier without breaking the warmed tortilla.

The laboratory results of enzymatic treatments were as follows:

| Corn tortilla texture: | Formula (3 = 1000, 2 = 100, 1 = 0 ppm): |
|---|---|
| Flexibility (rollability) | |
| 1-day | 3 > 2 > 1 |
| 7-days | 3 > 2 > 1 |
| Compressibility (elasticity) | |
| 1-day | 3 > 2 > 1 |
| 6-days | 3 > 2 > 1 |
| Rollability | |
| After 6-days | 1 > 3 = 2 |
| Moisture content (%) | |
| 7-days | 3 = 2 > 1 |

The tortilla treatments to which a high dosage of the enzyme blend (AM and RP & 1000 ppm) has been added were excellent in the standard laboratory evaluations in comparison with the control and enzyme A treatments. A low enzyme and specific actitivty in the crude extract A-blend, as compared to the commercial enzymes, might have caused a low flexibility-effect during tortilla storage.

Due to the addition of commercial enzymes during hydration of nixtamalized corn flour and dough kneading, flexibility, compressibility and rollability of the tortillas were improved. The acidic-activities of the arabinoxylans-depolymerizing enzymes of insoluble pericarp or fiber can be relatively low; nevertheless, they are believed to have a favorable impact on the tortillas due to rendering it more soluble-with water binding capacity- and a tendency to be softer (less elastic than the control).

The traditional-style tortilla is usually produced without additional use of gums, and therefore usually has a limited shelf-life because of microbial spoilage and staling as well. It is believed that hardening or loss of flexibility (35% after 4 days at room temperature), is caused by starch retrogradation. The addition of edible water-soluble alkaline materials (<1%; pH=8.5–9) to the corn dough markedly increased the yield of of dough (2.29) and tortilla (1.81) per kilogram of limed corn flour and retard spoilage (U.S. Pat. No. 3,730,732).

Thus a soluble corn-pericarp or bran may impart not only water binding capacity, but also cohesivity and plasticity to corn dough for traditional tortilla making. A corn masa dough model can be described as a plastic, cohesive, smooth mixture of large pieces of endosperm bound by a colloidal dispersion (5–9% of total dough). This glue-like dispersion is made of soluble starch, protein and non-starch polysaccharides which form a hydrated matrix where endosperm particles are suspended.

EXAMPLE 2

Preparation of mechanized tortillas, showing the effect of the enzyme blend on textural properties of corn packaged-tortillas.

A shelf-life test was performed on mechanized tortillas and stored at room temperature with standard laboratory evaluations made during their seven-day storage. Corn dough measurements before tortilla making included consistency (degree of resistance to penetration or firmness: Universal Penetrometer, Precision Scientific, Inc.) and adhesivity (ratio of adhesion breaking stress to cohesion breaking stress: U.S. Pat. No. 3,788,139). Plastic doughs which are soft and adhesive can be measured, thus making possible to determine the adhesion when the cohesion is known. Tortilla texture tests during storage comprised flexibility (resistance to bending with a method used in U.S. Pat. No. 3,730,732) and compressibility (resistance to compression with the same method as in Example 1). A higher flexibility index corresponds to rods of lower radii and indicates higher tortilla flexibility.

Mechanized tortilla pilot tests were carried out by adding to nixtamalized corn flour (commercially available type) a commercial water-soluble gum additive and two commercial enzyme blends: Formulation 1 (0 ppm or Control), Formulation 2 (Carboxymethylcellulose Sodium-Amtex, 2500 ppm), Formulation 3 (Amano-90, 100 ppm as recommended) and Formulation 4 (Hemicellulase-Rhodia, 1000 ppm).

The corn dough was mechanically made as follows: the corn flour and dry additives were mixed for 5 minutes (Dough mixer, Tecnomaíz-Gruma), warm potable water was added (1.2:1 ratio at 30° C.) with an antimicrobial acidic-additive (0.8% Kemin, based on flour) and the resulting corn dough was kneaded for 5 minutes.

Thereafter, the corn dough was moved and placed in a feeder-sheeting-former-oven machine (Rodotec Ecológica-100, Tecnomaíz-Gruma, Monterrey, N.L. México). A feed screw moves the dough horizontally into a manifold which pushes it through a slot. The plastic dough is fed onto a pair of smooth rollers, one rotating counterclockwise and the other clockwise. The gap between the rollers is adjustable and the thickness of the dough sheet determines the final product weight and its diameter.

The flat disks of dough pieces leave the front roller on a discharge belt, which feeds directly into the oven. A natural gas fired-oven is used to bake sheeted corn-dough into tortillas. They are baked at temperatures ranging from 300° C. to 330° C. in a multiple-pass three-tier oven in which the residence varies from 20–40 seconds. After cooling the tortillas (0.18 cm or 61–74 mils-thickness) at room temperature, they were packaged in polyethylene bags and sealed for storage.

Prior to kneading, the enzyme composition can be mixed with a portion of the total amount of corn masa flour to form a so-called tortilla pre-mixture. This pre-mixture can be added at the beginning of dough mixing in controlled dosages per kilogram of corn flour (Amano-90, 100 ppm and Hemicellulase-Rhodia, 1000 ppm). The carrier in the pre-mixture can also be other ingredients than corn flour, such as an anticaking agent or an antimicrobial acidic-addtives mixture containing ingredients and conventional additives. Dough made with enzyme formulation gave the following results:

| Corn dough machinability: | Formulation treatments: |
|---|---|
| Consistency (firmness) | 1 > 2 > 4 = 3 |
| 0-day | 148 to 165 |
| Adhesivity (stickiness) | 4 = 3 > 2 = 1 |
| 0-day | 0.4 to 0.6 |
| Moisture content (%) | 4 = 3 = 2 = 1 |
| 0-day | 58 to 59 |
| Surface roughness | 4 = 3 = 1 > 2 |
| Moisture baking loss (%) | 4 = 3 > 1 > 2 |
| 0-day | 17 to 20 |

-continued

| Corn dough machinability: | Formulation treatments: |
|---|---|
| Baking swelling (%) | 2 > 4 > 1 = 3 |
| 0-day | 75 to 89 |

Pilot-scale results from the tortilla making showed that the corn dough prepared with the addition of an enzyme composition was less firm and less cohesive after kneading than the conventional CMC (0.25%) and control dough. A similar moisture content among treatments indicated a more adhesive (but non-sticky) corn dough with enzyme blend as compared to the commercial CMC and control. Enzyme (AM) treatment of corn dough (at a constant moisture content) with excess level of xylanase and/or amylase activity resulted in a rapid loss of dough strength (less cohesive) and production of a wet, sticky dough mass.

The addition of enzyme blends acts to decrease the yield of corn dough per kilogram of corn flour, and the total amount of water used to make a standard consistency dough (regular type) is lower than if the additives were not employed. A higher dough consistency is proportional to its viscosity and to cohesive dough strength which holds the viscoelastic food under stress during tortilla making.

A low moisture content composition may result in a machinable (firm), cohesive (viscous) and non-sticky corn dough needed to shape flat disks into thin and rollable tortillas with a potential in reducing energy baking cost. Weak corn flours tend to give sticky doughs that hang up in the equipment with little cohesivity with which to bear its own weight if it is to form a sheet dough and not to break apart.

Corn masa dough texture is determined by factors such as maize variety, endosperm texture, drying conditions, as well as the water uptake and degree of starch gelatinization during corn cooking and grinding operations. During alkali-cooking, chemical and physical changes, such as gelatinization and partial removal of the germ and pericarp, occur in the corn kernel. During the formation of corn dough, grinding disrupts the swollen gelatinized starch granules and distributes the hydrated starch and protein around the ungelatinized portion of the corn endosperm.

Therefore a knowledge of corn flour characteristics as well as interactions among their components and other dough ingredients can be improved by understanding their critical properties. An evaluation of physicochemical and Theological properties of corn products has been a valuable tool for describing and predicting the quality of raw materials, intermediate and final products in processes. Objective tests which best predict the tortilla and snack making quality of U.S. and Mexican corn masa flours were particle size distribution, water uptake (dough yield), pH color and amylograph peak viscosity.

Differences observed during the baking process in the corn dough properties manifested themselves in the final mechanized tortilla product (50 tortillas per minute):

| Corn tortilla texture: | Formulation treatments: |
|---|---|
| Flexibility (rollability) | 4 = 3 = 2 > 1 |
| 7-days | 3 to 4.5 |
| Compressibility (%) | 4 = 3 = 2 > 1 |
| 7-days | 8 to 12 |

-continued

| Corn tortilla texture: | Formulation treatments: |
| --- | --- |
| Moisture content (%) | 4 = 3 = 2 = 1 |
| 7-days | 46 to 47 |
| Thickness (mils) | 4 = 3 = 2 > 1 |
| 7-days | 70 to 74 |

The pilot-scale tortillas showed that by means of the enzyme blend the machinability of the doughs could be improved with the exception of a rough tortilla surface as compared to the conventional CMC-additive (0.25% of water-soluble gum or hydrocolloid) used in commercial mechanized production (600 or 900 tortillas per minute).

The new enzyme additive (AM at 100 ppm or RP at 1000 ppm) imparts the novel property of retarding the loss of flexibility and compressibility in during a seven-day storage time. Thus, packaged tortillas with antimicrobial acidic-additives and stored at room temperature which no moisture is lost from them become hard or stale more slowly because of the enzyme blend, which increases the flexible shelf-life and the freshness of stored and also reheated tortillas.

The nixtamalized corn flour used in this invention (regular brand) can contain coarse, intermediate and fine particles. The large ones are pieces of remnant pericarp or bran, peripheral endosperm and germ. The medium and small particles are mostly endosperm and germ pieces. Thus, particle size distribution and moisture content in the formulation affect directly not only the physical-rheological properties of corn dough but also its machinability during tortilla making. A corn pericarp or bran may contain a 50% heteroxylan content and when it is extracted with alkali, yields from 30 to 45% have been reported. This corn soluble-fiber, commonly referred to as corn fiber gum or hydrocolloid (in dry and wet milling processes), has new functional properties as an adhesive, thickener, stabilizer and antistaling additive in high-moisture and packaged-foods such as, corn-tortilla (40 to 50%), wheat-bread (35 to 40%) and flour tortilla (30 to 35%).

Rubio (1973) described marked differences between wheat bread or flat-bread versus corn tortillas in relation to: their chemical composition, ingredients, dough making and baking. In addition to debranned and degermed wheat flour, the dough used for making high-moisture wheat products always contain more ingredients than corn tortilla where the base material is nixtamalized whole-corn or dry limed corn flour, with water and antimicrobial or functional alkaline-additives which can be mixed prior or after corn-dough preparation for increasing their shelf-life during four days at room temperature.

A partial enzymatic and acidic (ie., pH=5–5.5) hydrolysis of corn-pericarp or bran yielded oligosaccharide fragments rendering the insoluble dietary fiber into a soluble fiber which may develop an increased hydrated dough matrix (ie., 50 to 60% moisture), during mechanical kneading and baking, with better tolerance to dough sheeting and forming in mechanized tortilla making. The effective amount of arabinoxylan or heteroxylan hydrolytic enzymes is mutually dependent on the activities of each other. Furthermore, the levels may also be dependent on the microbial xylanase source (fungal or bacterial) used in industrial enzyme production and purification processes.

The enzyme blend additive of the present invention has the property of retarding loss of flexibility which is promoted by storing under refrigeration and freezing temperatures. Another conventional or antimicrobial acidic-additive used in the corn dough has the capacity of increasing resistance to microbial spoilage up to seven-day tortilla storage.

While the invention has been described above in connection with several preferred embodiments, it is to be expressly understood that those embodiments are solely for illustrating the invention, and are not to be construed in a limiting sense. After reading this disclosure, those skilled in this art will readily envision insubstantial modifications and substitutions of equivalent materials and techniques, and all such modifications and substitutions are considered to fall within the true scope of the appended claims.

We claim:

1. A method of making corn tortillas to be packaged that results in improved textural properties of the packaged tortillas after seven days comprising the steps of:
    a) providing nixtamalized corn flour comprising endosperm, germ, and at least one of pericarp and bran,
    b) mixing the nixtamalized corn flour with water and an effective amount of xylanase to form corn-dough, and
    c) baking the corn-dough to partially hydrolyze insoluble heteroxylans from the endosperm, the germ and at least one of the pericarp and bran cell-walls.

2. The method of claim 1 wherein the effective xylanase concentration is from about 100 mg to about 1000 mg per kilogram of nixtamalized corn flour.

3. The method of claim 1, wherein said dough further comprises antimicrobial acidic-additives in an amount of about 0.5% to about 1% by weight to retard spoilage.

4. The method in accordance to claim 2, wherein said xylanase operates delay to a loss of flexibility and compressibility after a seven-day storage of a packed-tortilla at ambient temperature.

5. The method of claim 3 wherein said mixing step further comprises mixing antimicrobial acidic-additives to said nixtamalized corn flour, said water, and said xylanase.

6. The method of claim 4 wherein said nixtamalized corn flour contains between 7% and 9% by weight of total dietary fiber and bran and from 6% to about 8% by weight of insoluble dietary fiber.

7. The method in accordance to claim 3, wherein said xylanase operates to delay a loss of flexibility and compressibility after a seven-day storage of a packed-tortilla at ambient temperature.

8. The method of claim 1, wherein a temperature during the baking step does not exceed a denaturing temperature of the xylanase.

* * * * *